United States Patent [19]

Uhing et al.

[11] 4,052,463
[45] Oct. 4, 1977

[54] PROCESS FOR PREPARING TERTIARY PHOSPHINE SULFIDES AND OXIDES

[75] Inventors: Eugene H. Uhing, Pleasantville, N.Y.; Arthur D. F. Toy, Stamford, Conn.

[73] Assignee: Stauffer Chemical Company, Westport, Conn.

[21] Appl. No.: 619,744

[22] Filed: Oct. 6, 1975

[51] Int. Cl.$^2$ .............................................. C07F 9/53
[52] U.S. Cl. .......................................... 260/606.5 P
[58] Field of Search ................................ 260/606.5 P

[56] References Cited

U.S. PATENT DOCUMENTS

| | | | |
|---|---|---|---|
| 2,542,370 | 2/1951 | Stevens et al. | 260/967 X |
| 2,731,458 | 1/1956 | Garwood et al. | 260/606.5 P |
| 2,819,290 | 1/1958 | McLeod | 260/967 X |
| 3,352,925 | 11/1967 | Hamilton | 260/606.5 P |
| 3,644,595 | 2/1972 | Wu | 260/920 |
| 3,660,539 | 5/1972 | Wu | 260/920 |
| 3,705,216 | 12/1972 | Farley | 260/606.5 P |

OTHER PUBLICATIONS

Chemical Abstracts, 51, 16364e (1957).
Chemical Abstracts, 65, 742b (1966).

*Primary Examiner*—Helen M. S. Sneed
*Attorney, Agent, or Firm*—William R. Robinson

[57] ABSTRACT

Tertiary phosphine sulfides and oxides are prepared by contacting elemental phosphorus with dialkyl sulfides, diaryl sulfides or dialkyl ethers in the presence of a catalyst under at least autogenous pressure at a temperature of from about 200° to about 400° C. The compounds obtained are useful as constituents in catalysts, insecticides, fungicides and pharmaceuticals, and as intermediates in preparation of other organophosphorus compounds.

7 Claims, No Drawings

PROCESS FOR PREPARING TERTIARY PHOSPHINE SULFIDES AND OXIDES

BACKGROUND OF THE INVENTION

1. Field of the Invention

The present invention relates to a new and improved process for the preparation of tertiary phosphine sulfides and oxides.

2. The Prior Art

Tertiary phosphine sulfides and oxides have been prepared in the prior art.

Methods of preparing tertiary phosphine sulfides are described in *Organic Phosphorus Compounds*, Vol. 4, G. M. Kosolapoff and L. Maier (John Wiley & Sons, Inc., 1972). These methods include, among others, the following reaction schemes:

$$R'_3P + S \rightarrow R'_3P(S) \tag{1}$$

$$P(S)Cl_3 + 3R'MgX \rightarrow R'_3P(S) + 3MgXCl \tag{2}$$

$$P(S)Cl_3 + 3R'Li \rightarrow R'_3P(S) + 3LiCl \tag{3}$$

$$P(S)Cl_3 + R'_3Al \rightarrow R'_3P(S) + AlCl_3 \tag{4}$$

wherein R' is a hydrocarbon group and X is halogen.

Methods of preparing tertiary phosphine oxides are described in *Organic Phosphorus Compounds*, Vol. 3, G. M. Kosolapoff and L. Maier (John Wiley & Sons, Inc., 1972). These methods include, among others, the following reaction schemes:

$$R'_3P + [O] \rightarrow R'_3P(O) \tag{5}$$

$$R'_4P^+OH^- \xrightarrow{decomposition} R'_3P(O) + R'H \tag{6}$$

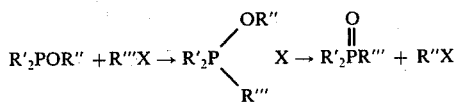

(9)

$$POCl_3 + 3R'MgX \rightarrow R'_3P(O) + 3MgXCl \tag{8}$$

wherein R', R'', and R''' are hydrocarbon groups and X is halogen.

SUMMARY OF THE INVENTION

In accordance with the present invention, there is provided a new method for preparing compounds of the formula:

(I)

wherein $R^{(1,2)}$ is a hydrocarbyl group or a mixture of hydrocarbyl groups consisting of hydrogen and carbon including $C_1$ to $C_7$ alkyl and the aryl (1 and 2 fused rings) substituted derivatives thereof, cycloalkyl of 5-6 carbons in the ring, aryl of up to 3 fused rings or biphenyl and the $C_1$–$C_4$ alkyl substituted derivatives of said cycloalkyl, aryl, or biphenyl and Z is sulfur or oxygen; provided that when Z is oxygen, $R^{(1,2)}$ is methyl. When Z is sulfur, however, the three hydrocarbyl groups represented by $R^{(1,2)}$ can be the same or different depending on starting materials as indicated below.

Typical alkyl groups include methyl, ethyl, n-propyl and isopropyl, n-butyl, isobutyl, tert-butyl, pentyl, hexyl and heptyl. Some suitable aralkyl groups are phenylmethyl, phenylethyl, phenylbutyl, phenyloctyl, phenylhexadecyl, and the corresponding naphthyl derivatives. Ring systems wherein $R^{(1,2)}$ is cycloalkyl having 5-6 carbons in the ring are illustrated by cyclopentyl and their derivatives.

Examples of aryl and substituted aryl groups include phenyl, methylphenyl, ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl, and the like. Any of said groups can contain one or more alkyl radicals and any isomeric form of said groups can be used.

Biphenyl $R^{(1,2)}$ groups include the $C_1$ to $C_4$ alkyl substituted derivatives such as methylbiphenyl and ditolyl. There can be one or more substituents as desired and said substituents can be in any isomeric position desired. The $R^{(1,2)}$ groups also can be connected to the phosphorus at any isomeric position.

The method of the present invention comprises contacting a reactant of the general formula:

$$R^1ZR^2 \tag{II}$$

wherein $R^1$ and $R^2$ are the same or different and have the same definition as $R^{(1,2)}$ as defined above and Z is as defined above with elemental phorphorus.

The following equation (9) is generally representative of the reaction:

$$6R^1ZR^2 + 4P \xrightarrow{catalyst} 3R_3^{(1,2)}\text{—}P(Z) + [R_3^{(1,2)}Z_3P] \tag{9}$$

where $[R_3^{(1,2)}Z_3P]$ represents a mixture of products including $(R^{(1,2)}Z)_3PZ$; $R_2^{(1,2)}P(Z)ZR^{(1,2)}$; $R^{(1,2)}P(Z)(ZR^{(1,2)})_2$ and dimers thereof. Of course, mixed reactants of the formula (II) can also be utilized.

Representative compounds within the formula (II) include dimethyl sulfide, methyl ethyl sulfide, methyl butyl sulfide, dipropyl sulfide, butyl disulfide, ethyl propyl sulfide, dipentyl sulfide, propyl butyl sulfide, hexyl heptyl sulfide, dihexyl sulfide, dicyclopentyl sulfide, dicyclohexyl sulfide, dibenzyl sulfide, ditolyl sulfide, diethylbenzyl sulfide, dipropylbenzyl sulfide, dibutylbenzyl sulfide, dinaphthyl sulfide, dimethylnaphthyl sulfide, diethylnaphthyl sulfide, dimethylanthryl sulfide, dibutylanthryl sulfide, dimethyl oxide and the like.

The foregoing compounds are given as illustrative and are in no way considered to be totally inclusive of all of the dialkyl and diaryl sulfides which can be used in the method of the present invention. Preparation of such sulfides and oxides is described in *Organic Phosphorus Compounds*, Volumes 3 and 4, G. M. Kosolapoff and L. Maier (John Wiley and Sons, Inc., 1972).

Various catalysts can be utilized in accordance with the reaction scheme of equation (9) above. These catalysts include iodine ($I_2$), alkyl halides such as $CH_3I$, $CH_3Cl$, and $C_2H_5I$, aryl halides such as $C_6H_5I$, iodide salts such as NaI and other halogen derivatives which are capable of opening the bonds of $P_4$ to give a more reactive intermediate and being regenerated after reacting.

When diaryl sulfide reactants are utilized, use of the catalyst is optional since the high thermal stability of diaryl sulfides allows reaction at high temperatures without a catalyst.

Use of the catalyst in this case, however, will facilitate the reaction at lower temperatures.

Reactants utilized in the process of the present invention can be employed in stiochiometric amounts, although an excess of either reactant can be used if desired.

The process of the present invention is carried out at elevated temperatures and at least at autogenous pressure and generally at a pressure of between about 1 and 700 atmospheres. Temperatures of from about 200° to about 400° C. can be used although temperatures of from about 250° to about 375° C. are preferred for the reaction to proceed to completion in a reasonable time.

Reaction times can vary over relatively wide ranges and can easily be determined by one skilled in the art. Factors affecting reaction time include reactivity of the reactants and temperature. For example, reactivity of dialkyl sulfides increases with chain length and reaction time therefore decreases accordingly. Reaction time generally decreases with increases in reaction temperature. Typical reaction times are from about 0.5 to about 24 hours.

The process of the present invention can conveniently be effected by introducing the individual reactants into a reaction zone capable of withstanding elevated pressure, such as a metal bomb, autoclave, or other pressure vessel, and carrying out the reaction under at least the autogenous pressure developed by the reactants at the reaction temperature. Pressures of up to about 700 atmospheres above the autogenous pressure can also be used but are less desirable due to the inconvenience and attendant dangers of requiring a pressurization system. An agitation means should be provided for said reaction zone. The reaction can be carried out in a continuous or batch-wise system as desired.

The products of the reaction are purified by conventional methods such as by fractional distillation of liquids and sublimation, crystallization, or extraction of solid products.

The identification of products is achieved by conventional methods, such as elemental analysis, and gas chromatography for purity and mass spectrometer and nuclear magnetic resonance and infrared analysis to establish structure.

Illustrative of the compounds which can be prepared by the method of the present invention are:
Alkyl:

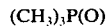

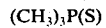

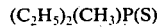

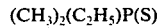

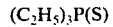

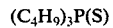

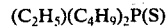

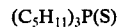

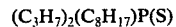

CYCLIC COMPOUNDS

Aromatic

Benzene:

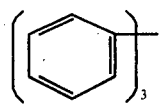

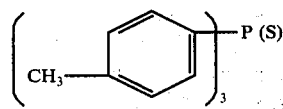

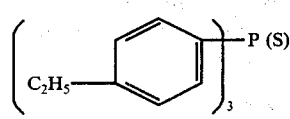

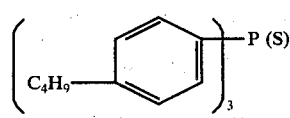

Naphthalene:

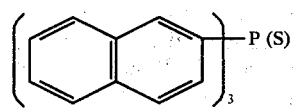

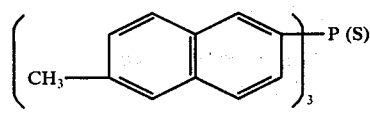

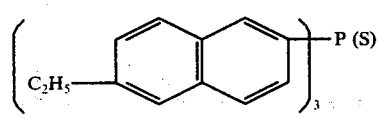

Anthracene:

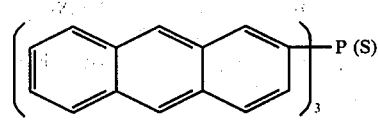

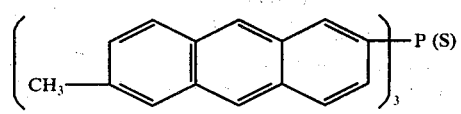

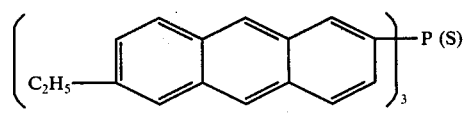

Biphenyl:

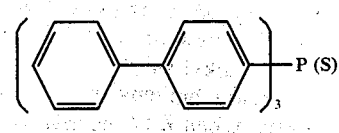

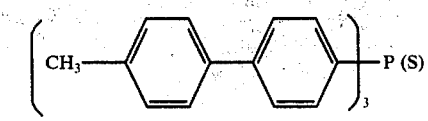

Cycloalkyl:
5 membered carbon ring:

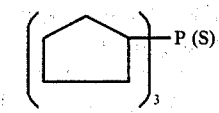

6 membered carbon ring:

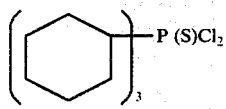

The products of the present invention, being sulfides or oxides of tertiary phosphine, can be used as intermediates to make trialkyl or triaryl phosphines. Such reactions are described in *Organic Phosphorus Compounds*, Volume 1, G. M. Kosolapoff and L. Maier (John Wiley and Sons, Inc., 1972) pp. 45–47.

Other uses of the products of the present invention as constituents in insecticides, fungicides and pharmaceuticals, and as intermediates in preparation of other organophosphorus compounds are known.

The present invention will be more fully illustrated in the Examples which follow.

EXAMPLE I

In a 40 milliliter glass Carius tube were placed 3.7 grams (0.06 mole) dimethyl sulfide and 1.5 grams (0.0484 gram atoms) yellow phosphorus. A small amount of iodine (about 0.01 gram) was then added. The carius tube was sealed and placed in a 300 milliliter high pressure autoclave (rated at 5000 psig) along with 40 milliliters chlorobenzene to equalize the pressure on the Carius tube. The autoclave was pressurized to 300 pounds per square inch gauge with $N_2$ before heating.

The autoclave was sealed and heated at 330° C. for 12 hours. After cooling the Carius tube was removed and opened. The tube contained a light brown solid. That solid was removed and dissolved in hot ethyl alcohol followed by filtration and vacuum distillation of the alcohol solution. A white solid residue was obtained. That residue was dissolved in hot cyclohexane followed by cooling and crystallization.

The crystals weighed 3.0 grams and were found by hydrogen nuclear magnetic resonance to be 90% $(CH_3)_3P(S)$. The melting point was 135°–143° C.

EXAMPLE II

In a 300 milliliter 316 stainless steel autoclave were placed 37.6 grams (0.61 moles) dimethyl sulfide and 15.7 grams (0.51 gram atoms) yellow phosphorus. A small amount of iodine (about 0.1 gram) was then added. The autoclave was sealed and provided with a nitrogen atmosphere.

The autoclave was heated at 330° C. for 12 hours. After cooling the autoclave was opened and 44.5 grams of a light brown crystalline solid were removed. A few long needles which had formed in the autoclave were isolated and were found to have a melting point of 153.5° C. The crude product was dissolved in 200 milliliters of hot ethyl alcohol followed by filtration and vacuum distillation of the alcohol solution. A white solid residue was obtained. The residue weighed 36.5 grams giving an 83% yield based on $(CH_3)_2S$. A 5 gram sample was sublimed to give 4.5 grams of pure $(CH_3)_3P(S)$.

EXAMPLE III

In a 300 milliliter 316 stainless steel autoclave were placed 54 grams (0.6 mole) diethyl sulfide and 15.6 grams (0.5 gram atoms) yellow phosphorus. A small amount of iodine (about 0.1 gram) was then added. The autoclave was sealed and provided with a nitrogen atmosphere.

The autoclave was heated at 295°–300° C. for 12 hours. After cooling the autoclave was opened and 61 grams of solid were removed. A red solid, 4.4 grams, was removed by filtration. The remaining crude product was distilled to give 13 grams of unreacted $(C_2H_5)_2S$ and 12 grams of $(C_2H_5)_3P(S)$ product with a boiling point of 100°–125° C. at 1.5 to 0.3 milliliters Hg. The distilled product crystallized on cooling and the crystals had a melting point of 93°–94° C. Analysis for phosphorus and sulfur was consistent with theoretical calculations for $(C_2H_5)_3P(S)$.

EXAMPLE IV

In a 40 milliliter glass Carius tube were placed 9.8 grams (0.053 mole) diphenyl sulfide and 1.4 grams (0.045 gram atoms) yellow phosphorus. The Carius tube was sealed and placed in a 300 milliliter autoclave along with 40 milliliters chlorobenzene to equalize the pressure on the Carius tube.

The autoclave was sealed and heated at 330° C. for 12 hours. After cooling the Carius tube was removed and opened. The crude product was removed and dissolved in hot ethyl alcohol followed by filtration. On cooling, 5.6 grams of solid precipitated out. This solid was recrystallized twice more from ethanol. The yield of triphenyl phosphine sulfide was 1.5 grams and had a melting point of 157.5°–158° C. Analysis for phosphorus and sulfur was consistent with theoretical calculations for triphenyl phosphine sulfide.

EXAMPLE V

In a 300 milliliter 316 stainless steel autoclave were placed 47.8 grams (0.257 mole) diphenyl sulfide and 6.8 grams (0.219 gram atoms) yellow phosphorus.

The autoclave was sealed under a nitrogen atmosphere and heated at 345° C. for 12 hours. After cooling the autoclave was opened and the crude product therein was washed with cold ethanol to remove the unreacted diphenyl sulfide. The washed product was dissolved in hot ethanol followed by filtration. The $(C_6H_5)_3P(S)$ product crystallized from the filtrate on cooling. The total yield of product was 31.8 grams (63% yield).

EXAMPLE VI

In a 40 milliliter Carius tube were placed 4.0 grams (0.087 mole) $(CH_3)_2O$ and 1.9 grams (0.0613 gram atoms) yellow phosphorus. A small amount of iodine (about 0.02 gram) was then added. The Carius tube was sealed while frozen at liquid nitrogen temperature and placed in a cold 300 milliliter autoclave along with 40 milliliters CH₂Cl₂ to equalize the pressure on the Carius tube. The autoclave was sealed and pressurized to 300 pounds per square inch gauge with nitrogen before heating.

The autoclave was heated at 330° C. for 12 hours. After cooling, the Carius tube was removed and opened. The tube lost 0.5 gram on venting and the crude product was dissolved in CHCl₃ followed by filtration. The CHCl₃ was removed, leaving 5.6 grams of crude product. This product was extracted with hot benzene to give 3.6 grams of soluble product. The benzene was removed and the solid product was sublimed to give 2.9 grams of (CH₃)₃P(O). Analysis by H-nuclear magnetic resonance, mass spectra and determination of percent phosphorus each confirmed that (CH₃)₃P(O) was produced.

EXAMPLE VII

In a 300 milliliter 316 stainless steel autoclave were placed 65 grams (1.4 moles) (CH₃)₂O and 29 grams (0.935 gram atoms) yellow phosphorus. A small amount of iodine (about 0.1 gram) was then added. The autoclave was sealed before heating at 325° C. for 8 hours. After cooling the autoclave was vented to release 6.0 grams unreacted (CH₃)₂O and 4.0 grams low boiling gas. The crude product was a sticky solid which was sublimed to give 33.5 grams of (CH₃)₃P(O).

EXAMPLE VIII

In a 300 milliliter 316 stainless steel autoclave were placed 42.0 grams (0.29 mole) (C₄H₉)₂S and 7.5 grams (0.24 gram atoms) yellow phosphorus. A small amount of iodine (about 0.1 gram) was then added. The autoclave was sealed before heating at 300° C. for 12 hours. After cooling and venting, 45.5 grams of crude product were removed. The crude product was distilled at 0.1 millimeters Hg pressure to give 15 grams of product having a boiling range of 130°–200° C. Analysis by ³¹P-nmr indicated that 26% of the phosphorus present had a chemical shift (ref H₃PO₄) of −47.8 ppm (literature value for (C₄H₉)₃P(S) = 48 ppm). The six other phosphorus components appeared to be mainly C₄H₉P(S)(SC₄H₉)₂, (C₄H₉)₂P(S)(S₄H₉) and isomers.

Having set forth the general nature and some examples of the present invention, the scope is now particularly set forth in the appended claims.

What is claimed is:

1. A method of preparing compounds of the formula:

wherein $R^{(1,2)}$ is selected from the group consisting of C₁ to C₇ alkyl; the aryl substituted derivatives thereof, said aryl substituted derivatives having 1 or 2 fused rings; cycloalkyl of 5 – 6 carbons in the ring; aryl of up to 3 fused rings; biphenyl and the C₁ to C₄ alkyl substituted derivatives of said cycloalkyl, aryl and biphenyl and Z is selected from the group consisting of sulfur and oxygen, provided that when Z is oxygen $R^{(1,2)}$ is methyl, comprising contacting under at least an autogenous pressure at a temperature of from about 200° C. to about 400° C. a reactant of the formula:

wherein $R^1$ and $R^2$ are the same or different and have the same definition as $R^{(1,2)}$ as defined above and Z is as defined above, with elemental phosphorus in the presence of a catalyst selected from the group consisting of iodine, alkyl halide, aryl halide and iodide salt.

2. The method of claim 1 wherein Z is sulfur and R is alkyl selected from the group consisting of methyl, ethyl, n-propyl, isopropyl, n-butyl, isobutyl, tert-butyl, pentyl, hexyl and heptyl.

3. The method of claim 1 wherein Z is sulfur and $R^{(1,2)}$ is aralkyl selected from the group consisting of phenylmethyl, phenylethyl, phenylbutyl, phenyloctyl, phenylhexadecyl, and the corresponding naphthyl derivatives.

4. The method of claim 1 wherein Z is sulfur and $R^{(1,2)}$ is cycloalkyl selected from the group consisting of cyclopentyl and cyclohexyl and derivatives thereof.

5. The method of claim 1 wherein Z is sulfur and $R^{(1,2)}$ is aryl selected from the group consisting of phenyl, methylphenyl, ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, dimethylphenyl, dimethylnaphthyl, diethylanthryl, biphenyl and derivatives thereof.

6. A method of preparing compounds of the formula:

wherein $R^{(1,2)}$ is selected from the group consisting of aryl, of up to 3 fused rings; biphenyl and the C₁–C₄ alkyl substituted derivatives of said aryl and biphenyl and Z is sulfur, comprising contacting under at least an autogenous pressure at a temperature of from about 200° C. to about 400° C. a reactant of the formula:

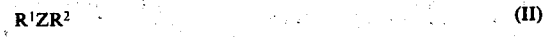

wherein $R^1$ and $R^2$ are the same or different and have the same definition as $R^{(1,2)}$ as defined above and Z is as defined above, with elemental phorphorus.

7. The method of claim 6 wherein $R^{(1,2)}$ is selected from the group consisting of phenyl, methylphenyl, ethylphenyl, propylphenyl, and butylphenyl, naphthyl, methylnaphthy, ethylnaphthyl, propylnaphthyl, butylnaphthyl, anthryl, methylanthryl, propylanthryl, butylanthryl, dimethylphenyl, dimethylnaphthyl, diethylanthryl, biphenyl and derivatives thereof.

* * * * *